(12) United States Patent
Zhang et al.

(10) Patent No.: US 12,287,304 B2
(45) Date of Patent: Apr. 29, 2025

(54) FLEXIBLE pH SENSOR AND DETECTION SYSTEM

(71) Applicant: Jiangnan University, Wuxi (CN)

(72) Inventors: Jie Zhang, Wuxi (CN); Fenglong Shang, Wuxi (CN); Fei Li, Wuxi (CN); Siqi Nan, Wuxi (CN); Xin Meng, Wuxi (CN); Baobing Zhang, Wuxi (CN); Tianwei Zhang, Wuxi (CN); Xuhui Wang, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 18/773,416

(22) Filed: Jul. 15, 2024

(65) Prior Publication Data

US 2024/0369509 A1    Nov. 7, 2024

Related U.S. Application Data

(63) Continuation of application No. PCT/CN2024/091382, filed on May 7, 2024.

(30) Foreign Application Priority Data

Nov. 20, 2023   (CN) .......................... 202311556759.3

(51) Int. Cl.
   *G01N 27/30*       (2006.01)
   *C25D 5/18*        (2006.01)
   (Continued)

(52) U.S. Cl.
   CPC .......... *G01N 27/302* (2013.01); *C25D 13/08* (2013.01); *C25D 15/00* (2013.01); *G01N 27/301* (2013.01);
   (Continued)

(58) Field of Classification Search
   None
   See application file for complete search history.

(56) References Cited

U.S. PATENT DOCUMENTS

| 5,250,163 A * | 10/1993 | Epstein ............. G01N 27/4167 205/787.5 |
| 2020/0116664 A1 * | 4/2020 | Abeyrathne ......... G01N 27/333 |

FOREIGN PATENT DOCUMENTS

| CN | 105606678 A | 5/2016 |
| CN | 117554447 A | 2/2024 |

(Continued)

OTHER PUBLICATIONS

Patil et al., Phys. Chem. Chem. Phys., 2012, 14, 11886-11895 (Year: 2012).*

(Continued)

*Primary Examiner* — Louis J Rufo
(74) *Attorney, Agent, or Firm* — IPRO, PLLC (57) ABSTRACT

Disclosed are a flexible pH sensor and detection system, belonging to the technical field of sensors. A material that does not react with electrolyte is mixed with metals to print an anode substrate, and one-step synthesis of a metal ions doped polyaniline composite material is realized through an electrochemical method. The doping amount of metal ions in polyaniline is changed by controlling metal content; due to addition of the metals, the conductivity of the anode substrate is improved, which is conducive to the deposition of polyaniline; such one-step method for preparing the polyaniline composite material is simpler, low in cost, and pollution-free; and compared with pure polyaniline, the sensitivity is further improved. According to the solution, this material is applied to the pH sensor for the first time, achieving a wide pH detection range (2-12) and high bending stability.

3 Claims, 1 Drawing Sheet

(51) Int. Cl.
*C25D 13/08* (2006.01)
*C25D 15/00* (2006.01)
*G01N 33/02* (2006.01)
*G01N 33/50* (2006.01)

(52) U.S. Cl.
CPC ............ *G01N 33/02* (2013.01); *G01N 33/50* (2013.01); *C25D 5/18* (2013.01)

(56) References Cited

FOREIGN PATENT DOCUMENTS

| | | | |
|---|---|---|---|
| EP | 3301686 A1 | 4/2018 | |
| KR | 20090113990 A | 11/2009 | |
| KR | 20180073868 A | 7/2018 | |
| KR | 20190083120 A * | 7/2019 | ........... C07D 273/00 |

OTHER PUBLICATIONS

Hui et al, J. Electrochem., vol. 22 Is. 1 pp. 64-69, 2016 (Year: 2016).*

* cited by examiner

FLEXIBLE pH SENSOR AND DETECTION SYSTEM

TECHNICAL FIELD

The present disclosure relates to a flexible pH sensor and detection system, belonging to the technical field of sensors.

BACKGROUND

A flexible pH sensor is a type of sensor capable of detecting the acidity or alkalinity of a solution or medium, consisting of a pH sensitive electrode and a pH reference electrode, where the pH sensitive electrode serves as a core component of the sensor and is prepared from a flexible substrate and a sensitive material. The detection principle lies in that the sensitive material on the pH sensitive electrode reacts with hydrogen ions to generate a potential difference proportional to the concentration of hydrogen ions (i.e., pH value), and the pH value of the solution or medium is then derived from the potential difference provided by the working and reference electrodes. Flexible pH sensors can adapt to application scenarios with different shapes and surfaces due to their good flexibility. The flexible pH sensors are generally used in biomedical, food industry, environmental monitoring and other fields, especially for the detection of pH values on curved or irregularly shaped surfaces.

A metal oxide is commonly used as the sensitive material for preparing the existing flexible pH sensor, but due to the fact that the metal oxides are usually found in the form of solid particles, the bending performance of the prepared pH sensor is poor, and the preparation process is relatively complicated. Polyaniline (PANI) is a conductive polymer, with nitrogen-containing monomeric units in its structure being capable of accepting or releasing protons ($H^+$) at different pH values: in an acidic environment, the nitrogen atom sites of polyaniline can be protonated to form positively charged $NH^+$ groups, which leads to electrostatic repulsion between polymer chains, thus increasing the electrical conductivity of the polymer; and conversely, in an alkaline environment, the protons are released, and the electrostatic repulsion between the polymer chains is reduced, resulting in polymer shrinkage and electrical conductivity reduction. Moreover, polyaniline, as a polymer, has good flexibility and good processability, and can be easily synthesized through various methods such as chemical or electrochemical methods. Therefore, it is suitable for flexible sensor structures with curved surfaces and bends.

Although polyaniline has better electrical conductivity and pH sensing performance, and is also better in flexibility, lower in preparation cost, simpler in preparation method and higher in pH sensing performance compared with metal oxides, but a single polyaniline material has lower pH sensitivity, so most of the current research on polyaniline-based pH sensors focuses on composite materials. There are two main types of composites available for pH sensing. One of them is obtained by doping polyaniline with a metal oxide, and the metal oxide improves the conductivity of the polyaniline to a certain extent. However, the preparation method (such as an electrochemical polymerization method, a sol-gel method, or a hydrothermal synthesis method) of metal oxide doped polyaniline is complex and costly to make pH sensor with poor bending properties. The other one is obtained by doping polyaniline with metal ions, and silver ions are preferred because of their higher conductivity and bactericidal performance. At present, the doping method of silver ions is mainly to add silver nitrate into an electrolyte solution or to soak the prepared polyaniline in a silver nitrate solution, both of which use silver nitrate as the source of silver ions, while silver nitrate is explosive and thus belongs to the controlled goods, which is not conducive to experimental safety and environmental protection, and cannot be applied to the food industry.

SUMMARY

In order to solve at least one of the above problems, the present disclosure provides a flexible pH sensor and detection system. The technical solutions are described below.

The first object of the present disclosure is to provide a preparation method for a flexible pH sensor. The flexible pH sensor includes a pH sensitive electrode and a pH reference electrode. The preparation of the pH sensitive electrode includes:

step (1): preparing a first electrode by printing a composite conductive material on a flexible substrate, where the composite conductive material is composed of two conductive materials, and the two conductive materials are denoted as a conductive material A and a conductive material B, respectively; and step (2): preparing an electrolyte solution containing acid and aniline, adopting cyclic voltammetry to prepare a polyaniline/cation composite material by using the first electrode prepared in step (1) as a working electrode in combination with the reference electrode and an counter electrode, and drying to obtain the pH sensitive electrode.

In one embodiment, the conductive material A is a material that does not react with electrolyte and serves as a growth substrate for polyaniline; and the conductive material B is an insoluble and easily electrolyzed material and is oxidized after being applied with voltage so as to provide cations for polyaniline.

In one embodiment, the material that does not react with the electrolyte includes carbon, FTO, platinum, and gold.

In one embodiment, the insoluble and easily electrolyzed material includes one or more of silver, gold, aluminum, iron, tungsten, zinc, and calcium; and further, the insoluble and easily electrolyzed material is powder, slurry, or in an ionic state in a solution.

In one embodiment, the mass ratio of the material that does not react with the electrolyte to the insoluble and easily electrolyzed material is (3-20): 1.

In one embodiment, the acid contained in the electrolyte solution prepared in step (2) is one of sulfuric acid, hydrochloric acid, phosphoric acid, oxalic acid, dodecylbenzene sulfonic acid, or salicylic acid.

In one embodiment, when the acid contained in the electrolyte solution prepared in step (2) is sulfuric acid, the content of sulfuric acid is 0.15-0.7 mol/L, and the content of aniline is 0.15-0.7 mol/L.

In one embodiment, the reference electrode in step (2) is one of mercurous sulfate, silver/silver chloride, a calomel electrode, mercury/mercuric oxide, and copper/copper sulfate.

In one embodiment, the counter electrode in step (2) is one of a platinum wire, nickel, tungsten, lead, and glassy carbon.

In one embodiment, the conditions of the cyclic voltammetry adopted in the step (2) are that the voltage range is −0.2 to 1.2 V, the scanning speed is 10-100 mV/s, and the number of cycles is greater than 4 times.

In one embodiment, the drying condition in step (2) is drying in an oven at 150° C. or below.

In one embodiment, a preparation process of the pH reference electrode includes: preparing a second electrode by using a flexible thin film as a substrate in combination with a conductive material; adopting cyclic voltammetry to prepare a silver/silver chloride reference electrode in a solution containing hydrochloric acid by using the second electrode as a working electrode, silver/silver chloride as a reference electrode, and a platinum wire as an counter electrode; and then, mixing polyvinyl alcohol with potassium chloride, stirring, coating the silver/silver chloride reference electrode with the obtained mixture dropwise, freezing to obtain a silver/silver chloride reference electrode covered with gel electrolyte, and drying to obtain the pH reference electrode.

In one embodiment, the content of hydrochloric acid used in the preparation process of the pH reference electrode is 0.098 mol/L.

In one embodiment, during the preparation process of the pH reference electrode, the reference electrode is commercial silver/silver chloride, a calomel electrode, mercury/mercuric oxide, or copper/copper sulfate.

In one embodiment, during the preparation process of the pH reference electrode, the counter electrode is one of a platinum wire, nickel, tungsten, lead, or glassy carbon.

In one embodiment, the conditions of the cyclic voltammetry are that the voltage range is 0 to 0.2 V, the scanning speed is 20-40 mV/s, and the number of cycles is 2-4 times.

In one embodiment, the mass ratio of polyvinyl alcohol to potassium chloride is (0.5-1.5): 1.

In one embodiment, the stirring condition is stirring for 3-5 h at 75-85° C.

In one embodiment, the freezing is to freeze for 4-6 h at −26 to −24° C. so as to obtain the silver/silver chloride reference electrode covered with gel electrolyte, and the drying is carried out in an oven at 70° C.

The second object of the present disclosure is to provide a flexible pH sensor prepared by the above-mentioned preparation method.

The third object of the present disclosure is to provide a flexible pH detection system, and the flexible pH detection system includes the above-mentioned flexible pH sensor, an external circuit, and a program development and interface;

the external circuit achieves a connection between the pH sensor and an analog-to-digital conversion module with an external wire, the connection part therebetween is fixed by spot welding, the analog-to-digital conversion module is connected to a development board by ways of a wire, and the analog quantity is transmitted to the development board and converted into data quantity; and the program development and interface is configured to compute and process the data quantity and output the data quantity as a pH value, establish a connection with a mobile phone through communication module, and develop and design a mobile phone interface to display pH value results.

The fourth object of the present disclosure is to provide a pH sensing test paper, and the pH sensing test paper is prepared based on the above-mentioned flexible pH sensor.

The fifth object of the present disclosure is to provide applications of the above-mentioned flexible pH sensor in saliva pH detection for reflecting oral health conditions, and in freshness detection of fresh food.

The present disclosure has the following beneficial effects.

The present disclosure uses the composite conductive material composed of the material which does not react with electrolyte and the insoluble and easily electrolyzed material metals to print the substrate of the pH sensitive electrode, and one-step synthesis of the metal-doped polyaniline composite material is realized through an electrochemical method. The doping amount of metal ions in polyaniline is changed by controlling metal content. The mixed substrate of the composite conductive material is used as the working electrode in the electrochemical synthesis process. After the working electrode undergoes an oxidation reaction, the aniline in the electrolyte solution is oxidized into polyaniline, and meanwhile, the metal elements in the mixed substrate are oxidized to metal ions and then enabled to enter the electrolyte solution. In the synthesis process of polyaniline, the metal ions are doped onto the imine nitrogen atoms of polyaniline and deposited on the working electrode together with polyaniline. When the content of the doped metals increases, the oxidized metals increase, and thus the metal ions doped onto the polyaniline increase; and therefore, the pH sensing performance of the polyaniline is affected. Due to addition of the metals, the conductivity of the anode substrate is improved, which is conducive to the deposition of polyaniline; such one-step method for preparing the polyaniline composite material is simpler, low in cost, and pollution-free; and the pH sensitivity of pure polyaniline is 52.47 mV/pH, and the reaction time at pH 4-8 is 41 s. The pH sensitivity can be effectively improved after doping polyaniline with metal ions, and thus the reaction time is significantly shortened. For example, the relative pH sensitivity is 130.2% after doping polyaniline with silver ions, and the reaction time at pH 4-8 is 10 s.

The material prepared according to the present disclosure is applied to the pH sensor for the first time, achieving a wide pH detection range (2-12) and high bending stability. Finally, all-solid pH sensing test paper is integrated, pH data can be displayed on a mobile phone terminal by ways of signal processing and transmission circuits, and the test paper is successfully applied to saliva pH detection for reflecting oral health conditions, and to freshness detection of fresh food.

BRIEF DESCRIPTION OF FIGURES

In order to more clearly illustrate the technical solutions in the examples of the present disclosure, the drawings needed to be used in the description of the examples will be briefly introduced below. Apparently, the drawings in the following description are only some examples of the present disclosure. For those of ordinary skill in the art, other drawings can also be obtained based on these drawings without making creative efforts.

DETAILED DESCRIPTION

In order to make the objects, technical solutions and advantages of the present disclosure clearer, the embodiments of the present disclosure will be described in further detail below with reference to the accompanying drawings.

The test methods involved in the present application are as follows:

(1) Relative Sensitivity:

Potential signals were collected by separately immersing a sensor in buffer solutions with pH values of 2, 4, 6, 8, 10, and 12. Each of the potential signals was obtained by measuring the potential difference between a working electrode and a reference electrode through an electrochemical workstation. The potential reading of the sensor at each of the pH values was recorded for linear fitting, and the obtained straight slope was the sensitivity of the sensor, measured in mV/pH.

In the case where the pH sensitivity of polyaniline prepared using a carbon substrate was considered as 100%, the sensitivities of sensors prepared in other examples were compared therewith so as to obtain different percentages as relative sensitivity values.

(2) pH Detection Range:

When the change in the measured potential values was linearly related to the change in the pH value, the pH value was considered to be within the measurable pH range of the sensor, and the maximum measurable pH range was considered to be the pH detection range.

(3) High Bending Stability:

The sensor was attached to the middle of a transparent film by using a stepper motor, and was driven to carry out a cyclic bending test at a fixed bending angle by ways of the motor. After the sensor was bent at a certain angle on a built platform for a certain number of times, it was placed in the buffer solutions with the different pH values, and the potentials in all states were recorded through potential measurement. The bending stability of the sensor was evaluated by comparing the change degrees of the potentials obtained under different bending times and different bending angles at the same pH value.

(4) Response Time:

The response time of a pH sensor was defined as the transmission time required for its potential reaching 90% of the equilibrium value after the sensor is immersed in buffer solutions with different pH values. The test is a change process of pH 4-8-4. The response time of pure polyaniline at pH 4-8 is 41 s, and the response time thereof at pH 8-4 is 48 s.

Example 1

Figure 1:
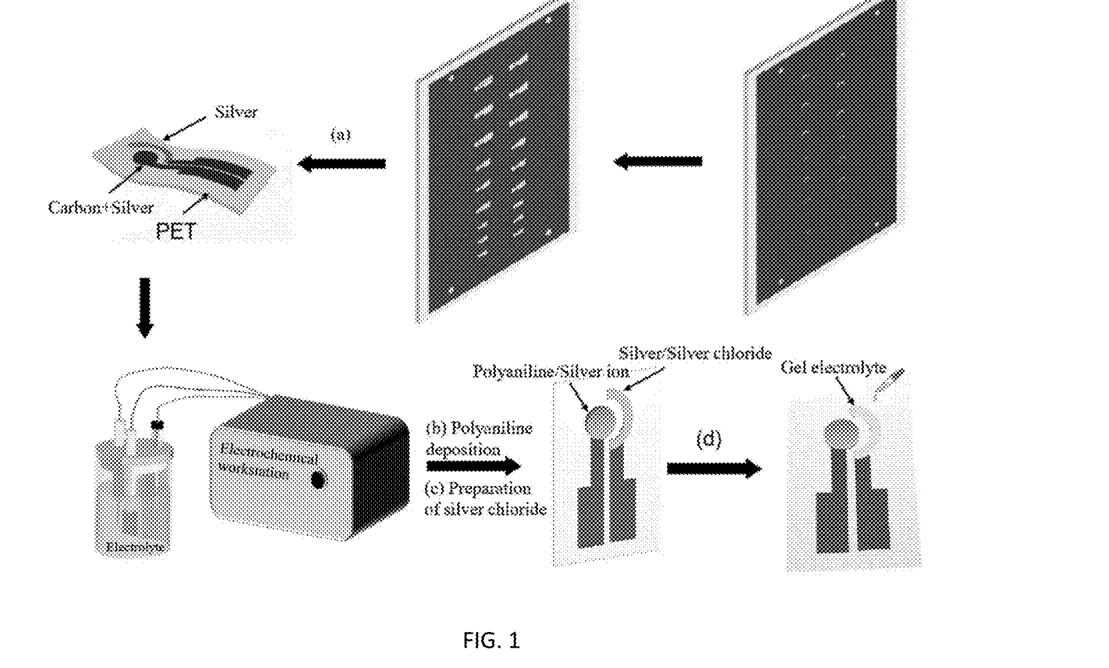
FIG. 1 is a flow chart for the preparation of a flexible pH sensor according to the present disclosure.

This example provides a preparation method for a flexible pH sensor. The flexible pH sensor includes a pH sensitive electrode and a pH reference electrode. Referring to FIG. 1, the method includes the following steps:

Step (1): Printing Electrodes

As shown in (a) of FIG. 1, composite paste formed by doping carbon paste with 10% (w/w) silver paste was printed as a first electrode, and then silver paste was stirred to be overprinted as a second electrode, where a printing substrate used was a flexible PET thin film; and that was to say, the first electrode was obtained by printing the composite paste of carbon paste and silver paste on the flexible PET thin film, and the second electrode was obtained by printing silver paste.

Step (2): Preparation of pH Sensitive Electrode

As shown in (b) of FIG. 1, 50 ml of an electrolyte solution containing 2.54 g of sulfuric acid and 1.17 g of aniline was prepared. In an electrochemical workstation, cyclic voltammetry was adopted to prepare a polyaniline/silver ion composite material by using the first electrode prepared in step (1) as a working electrode, mercurous sulfate as a reference electrode, and a platinum wire as an counter electrode; the voltage was set to be within a range of −0.2 to 1.2 V, the scanning speed was 40-80 mV/s, and the number of cycles was 6-12 times; and the polyaniline/silver ion composite material was dried in an oven at 50-100° C. so as to obtain a pH sensitive electrode.

With respect to the scanning speed, the number of cycles and the subsequent oven temperature in the cyclic voltammetry during the preparation process of the pH sensitive electrode, this example conducted multiple experiments with different values, and finally the average value was taken as shown in Table 1.

During the experimental process, it was found that the scanning speed, the number of cycles and the subsequent oven temperature had a relatively small impact on the preparation of the polyaniline/silver ion composite materials in cyclic voltammetry. Therefore, the scanning speed might be set to 10-100 mV/s, the number of cycles was greater than 4 times, and the subsequent oven temperature might be set to 150° C. or below.

Step (3): Preparation of pH Reference Electrode

As shown in (c) of FIG. 1, the second electrode prepared in step (1) was used as a working electrode, commercial silver/silver chloride was used as a reference electrode, and a platinum wire was used as an counter electrode; in 50 ml of a solution containing 0.48 g of hydrochloric acid, the voltage was set to be within a range of 0 to 0.2 V, and the scanning speed was set to 40 mV/s, with 4 cycles; then, as shown in (d) of FIG. 1, polyvinyl alcohol and potassium chloride were mixed together in a ratio of 1:1 (w/w), the mixture was stirred at 80° C. for 4 h, and the reference electrode was coated with the obtained mixture dropwise and frozen at −26° C. for 4 h to obtain a silver/silver chloride reference electrode covered with gel electrolyte; and the product was dried in an oven at 70° C. to prepare a pH reference electrode.

The flexible pH sensor was prepared by using the pH sensitive electrode obtained in step (2) and the pH reference electrode obtained in step (3).

Example 2

This example provides a preparation method for a flexible pH sensor. The flexible pH sensor includes a pH sensitive electrode and a pH reference electrode. Referring to FIG. 1, the method includes the following steps:

Step (1): Printing Electrodes

As shown in (a) of FIG. 1, composite paste formed by doping carbon paste with 20% (w/w) silver paste was printed as a first electrode, and then silver paste was stirred to be overprinted as a second electrode, where a printing substrate used was a flexible PET thin film; and that was to say, the first electrode was obtained by printing the composite paste of carbon paste and silver paste on the flexible PET thin film, and the second electrode was obtained by printing silver paste.

Step (2): Preparation of pH Sensitive Electrode

As shown in (b) of FIG. 1, 50 ml of an electrolyte solution containing 2.54 g of sulfuric acid and 1.17 g of aniline was prepared. In an electrochemical workstation, cyclic voltammetry was adopted to prepare a polyaniline/silver ion composite material by using the first electrode prepared in step (1) as a working electrode, mercurous sulfate as a reference electrode, and a platinum wire as an counter electrode; the voltage was set to be within a range of −0.2 to 1.2 V, the scanning speed was 40-80 mV/s, and the number of cycles was 6-12 times; and the polyaniline/silver ion composite material was dried in an oven at 50-100° C. so as to obtain a pH sensitive electrode.

With respect to the scanning speed, the number of cycles and the subsequent oven temperature in the cyclic voltammetry during the preparation process of the pH sensitive electrode, this example conducted multiple experiments with different values, and finally the average value was taken as shown in Table 1.

Step (3): Preparation of pH Reference Electrode

As shown in (c) of FIG. 1, the second electrode prepared in step (1) was used as a working electrode, commercial silver/silver chloride was used as a reference electrode, and a platinum wire was used as an counter electrode; in 50 ml of a solution containing 0.48 g of hydrochloric acid, the voltage was set to be within a range of 0 to 0.2 V, and the scanning speed was set to 40 mV/s, with 4 cycles; then, as shown in (d) of FIG. 1, polyvinyl alcohol and potassium chloride were mixed together in a ratio of 1:1 (w/w), the mixture was stirred at 80° C. for 4 h, and the reference electrode was coated with the obtained mixture dropwise and frozen at −24° C. for 6 h to obtain a silver/silver chloride reference electrode covered with gel electrolyte; and the product was dried in an oven at 70° C. to prepare a pH reference electrode.

The flexible pH sensor was prepared by using the pH sensitive electrode obtained in step (2) and the pH reference electrode obtained in step (3).

Example 3

This example provides a preparation method for a flexible pH sensor. The flexible pH sensor includes a pH sensitive electrode and a pH reference electrode. Referring to FIG. 1, the method includes the following steps:

Step (1): Printing Electrodes

As shown in (a) of FIG. 1, composite paste formed by doping carbon paste with 10% (w/w) silver paste was printed as a first electrode, and then silver paste was stirred to be overprinted as a second electrode, where a printing substrate used was a flexible PET thin film; and that was to say, the first electrode was obtained by printing the composite paste of carbon paste and silver paste on the flexible PET thin film, and the second electrode was obtained by printing silver paste.

Step (2): Preparation of pH Sensitive Electrode

As shown in (b) of FIG. 1, 50 ml of an electrolyte solution containing 0.74 g of sulfuric acid and 0.71 g of aniline was prepared. In an electrochemical workstation, cyclic voltammetry was adopted to prepare a polyaniline/silver ion composite material by using the first electrode prepared in step (1) as a working electrode, mercurous sulfate as a reference electrode, and a platinum wire as an counter electrode; the voltage was set to be within a range of −0.2 to 1.2 V, the scanning speed was 40-80 mV/s, and the number of cycles was 6-12 times; and the polyaniline/silver ion composite material was dried in an oven at 50-100° C. so as to obtain a pH sensitive electrode.

With respect to the scanning speed, the number of cycles and the subsequent oven temperature in the cyclic voltammetry during the preparation process of the pH sensitive electrode, this example conducted multiple experiments with different values, and finally the average value was taken as shown in Table 1.

Step (3): Preparation of pH Reference Electrode

As shown in (c) of FIG. 1, the second electrode prepared in step (1) was used as a working electrode, commercial silver/silver chloride was used as a reference electrode, and a platinum wire was used as an counter electrode; in 50 ml of a solution containing 0.48 g of hydrochloric acid, the voltage was set to be within a range of 0 to 0.2 V, and the scanning speed was set to 40 mV/s, with 4 cycles; then, as shown in (d) of FIG. 1, polyvinyl alcohol and potassium chloride were mixed together in a ratio of 1:1 (w/w), the mixture was stirred at 80° C. for 4 h, and the reference electrode was coated with the obtained mixture dropwise and frozen at −24° C. for 6 h to obtain a silver/silver chloride reference electrode covered with gel electrolyte; and the product was dried in an oven at 70° C. to prepare a pH reference electrode.

The flexible pH sensor was prepared by using the pH sensitive electrode obtained in step (2) and the pH reference electrode obtained in step (3).

Example 4

This example provides a preparation method for a flexible pH sensor. The flexible pH sensor includes a pH sensitive electrode and a pH reference electrode. Referring to FIG. 1, the method includes the following steps:

Step (1): Printing Electrodes

As shown in (a) of FIG. 1, carbon paste doped with 10% (w/w) tungsten powder was printed as a first electrode, and then silver paste was stirred to be overprinted as a second electrode, where a printing substrate used was a flexible PET thin film; and that was to say, the first electrode was obtained by printing the composite paste of carbon paste and tungsten powder on the flexible PET thin film, and the second electrode was obtained by printing silver paste.

Step (2): Preparation of pH Sensitive Electrode

As shown in (b) of FIG. 1, 50 ml of an electrolyte solution containing 1.27 g of sulfuric acid and 2.33 g of aniline was prepared. In an electrochemical workstation, cyclic voltammetry was adopted to prepare a polyaniline/tungsten ion composite material by using the first electrode prepared in step (1) as a working electrode, mercurous sulfate as a reference electrode, and a platinum wire as an counter electrode; the voltage was set to be within a range of −0.2 to 1.2 V, the scanning speed was 40-80 mV/s, and the number of cycles was 6-12 times; and the polyaniline/tungsten ion composite material was dried in an oven at 50-100° C. so as to obtain a pH sensitive electrode.

With respect to the scanning speed, the number of cycles and the subsequent oven temperature in the cyclic voltammetry during the preparation process of the pH sensitive electrode, this example conducted multiple experiments with different values, and finally the average value was taken as shown in Table 1.

Step (3): Preparation of pH Reference Electrode

As shown in (c) of FIG. 1, the second electrode prepared in step (1) was used as a working electrode, commercial silver/silver chloride was used as a reference electrode, and a platinum wire was used as an counter electrode; in 50 ml of a solution containing 0.48 g of hydrochloric acid, the voltage was set to be within a range of 0 to 0.2 V, and the scanning speed was set to 20 mV/s, with 2 cycles; then, as shown in (d) of FIG. 1, polyvinyl alcohol and potassium chloride were mixed together in a ratio of 1:1 (w/w), the mixture was stirred at 80° C. for 4 h, and the reference electrode was coated with the obtained mixture dropwise and frozen at −26° C. for 4 h to obtain a silver/silver chloride reference electrode covered with gel electrolyte; and the product was dried in an oven at 70° C. to prepare a pH reference electrode.

The flexible pH sensor was prepared by using the pH sensitive electrode obtained in step (2) and the pH reference electrode obtained in step (3).

Example 5

This example provides a preparation method for a flexible pH sensor. The flexible pH sensor includes a pH sensitive electrode and a pH reference electrode. Referring to FIG. 1, the method includes the following steps:

Step (1): Printing Electrodes

As shown in (a) of FIG. 1, carbon paste doped with 10% (w/w) zinc powder was printed as a first electrode, and then silver paste was stirred to be overprinted as a second electrode, where a printing substrate used was a flexible PET thin film; and that was to say, the first electrode was obtained by printing the composite paste of carbon paste and zinc powder on the flexible PET thin film, and the second electrode was obtained by printing silver paste.

Step (2): Preparation of pH Sensitive Electrode

As shown in (b) of FIG. 1, 50 ml of an electrolyte solution containing 1.27 g of sulfuric acid and 2.33 g of aniline was prepared. In an electrochemical workstation, cyclic voltammetry was adopted to prepare a polyaniline/zinc ion composite material by using the first electrode prepared in step (1) as a working electrode, mercurous sulfate as a reference electrode, and a platinum wire as an counter electrode; the voltage was set to be within a range of $-0.2$ to $1.2$ V, the scanning speed was 40-80 mV/s, and the number of cycles was 6-12 times; and the polyaniline/zinc ion composite material was dried in an oven at 50-100° C. so as to obtain a pH sensitive electrode.

With respect to the scanning speed, the number of cycles and the subsequent oven temperature in the cyclic voltammetry during the preparation process of the pH sensitive electrode, this example conducted multiple experiments with different values, and finally the average value was taken as shown in Table 1.

Step (3): Preparation of pH Reference Electrode

As shown in (c) of FIG. 1, the second electrode prepared in step (1) was used as a working electrode, commercial silver/silver chloride was used as a reference electrode, and a platinum wire was used as an counter electrode; in 50 ml of a solution containing 0.48 g of hydrochloric acid, the voltage was set to be within a range of 0 to 0.2 V, and the scanning speed was set to 20 mV/s, with 2 cycles; then, as shown in (d) of FIG. 1, polyvinyl alcohol and potassium chloride were mixed together in a ratio of 1:1 (w/w), the mixture was stirred at 80° C. for 4 h, and the reference electrode was coated with the obtained mixture dropwise and frozen at $-26$° C. for 4 h to obtain a silver/silver chloride reference electrode covered with gel electrolyte; and the product was dried in an oven at 70° C. to prepare a pH reference electrode.

The flexible pH sensor was prepared by using the pH sensitive electrode obtained in step (2) and the pH reference electrode obtained in step (3).

Example 6

This example provides a preparation method for a flexible pH sensor. The flexible pH sensor includes a pH sensitive electrode and a pH reference electrode. Referring to FIG. 1, the method includes the following steps:

Step (1): Printing Electrodes

As shown in (a) of FIG. 1, carbon paste was printed as a first electrode, and then silver paste was stirred to be overprinted as a second electrode, where a printing substrate used was a flexible PET thin film; and that was to say, the first electrode was obtained by printing carbon paste on the flexible PET thin film, and the second electrode was obtained by printing silver paste.

Step (2): Preparation of pH Sensitive Electrode

As shown in (b) of FIG. 1, 50 ml of an electrolyte solution containing 1.27 g of sulfuric acid, 2.33 g of aniline, and 0.56 g of calcium chloride was prepared. In an electrochemical workstation, cyclic voltammetry was adopted to prepare a polyaniline/calcium ion composite material by using the first electrode prepared in step (1) as a working electrode, mercurous sulfate as a reference electrode, and a platinum wire as an counter electrode; the voltage was set to be within a range of $-0.2$ to $1.2$ V, the scanning speed was 40-80 mV/s, and the number of cycles was 6-12 times; and the polyaniline/calcium ion composite material was dried in an oven at 50-100° C. so as to obtain a pH sensitive electrode.

With respect to the scanning speed, the number of cycles and the subsequent oven temperature in the cyclic voltammetry during the preparation process of the pH sensitive electrode, this example conducted multiple experiments with different values, and finally the average value was taken as shown in Table 1.

Step (3): Preparation of pH Reference Electrode

As shown in (c) of FIG. 1, the second electrode prepared in step (1) was used as a working electrode, commercial silver/silver chloride was used as a reference electrode, and a platinum wire was used as an counter electrode; in 50 ml of a solution containing 0.48 g of hydrochloric acid, the voltage was set to be within a range of 0 to 0.2 V, and the scanning speed was set to 20 mV/s, with 2 cycles; then, as shown in (d) of FIG. 1, polyvinyl alcohol and potassium chloride were mixed together in a ratio of 1:1 (w/w), the mixture was stirred at 80° C. for 4 h, and the reference electrode was coated with the obtained mixture dropwise and frozen at $-26$° C. for 4 h to obtain a silver/silver chloride reference electrode covered with gel electrolyte; and the product was dried in an oven at 70° C. to prepare a pH reference electrode.

The flexible pH sensor was prepared by using the pH sensitive electrode obtained in step (2) and the pH reference electrode obtained in step (3).

Example 7

This example provides a preparation method for a flexible pH sensor. The flexible pH sensor includes a pH sensitive electrode and a pH reference electrode. Referring to FIG. 1, the method includes the following steps:

Step (1): Printing Electrodes

A 100 nm gold film was prepared on a PET substrate using an vapor deposition as a first electrode, and then silver paste was stirred to be overprinted as a second electrode, where the printing substrate used was a flexible PET thin film.

Step (2): Preparation of pH Sensitive Electrode

As shown in (b) of FIG. 1, 50 ml of an electrolyte solution containing 2.45 g of sulfuric acid and 2.35 g of aniline was prepared. In an electrochemical workstation, cyclic voltammetry was adopted to prepare polyaniline by using the first electrode prepared in step (1) as a working electrode, mercurous sulfate as a reference electrode, and a platinum wire as an counter electrode; the voltage was set to be within a range of $-0.2$ to $1.2$ V, the scanning speed was 40-80 mV/s, and the number of cycles was 6-12 times; and the polyaniline was dried in an oven at 50-100° C. so as to obtain a pH sensitive electrode.

With respect to the scanning speed, the number of cycles and the subsequent oven temperature in the cyclic voltammetry during the preparation process of the pH sensitive electrode, this example conducted multiple experiments with different values, and finally the average value was taken as shown in Table 1.

Step (3): Preparation of pH Reference Electrode

As shown in (c) of FIG. 1, the second electrode prepared in step (1) was used as a working electrode, commercial silver/silver chloride was used as a reference electrode, and a platinum wire was used as an counter electrode; in 50 ml of a solution containing 0.48 g of hydrochloric acid, the voltage was set to be within a range of 0 to 0.2 V, and the scanning speed was set to 40 mV/s, with 4 cycles; then, as shown in (d) of FIG. 1, polyvinyl alcohol and potassium chloride were mixed together in a ratio of 1:1 (w/w), the mixture was stirred at 80° C. for 4 h, and the reference electrode was coated with the obtained mixture dropwise and frozen at −24° C. for 6 h to obtain a silver/silver chloride reference electrode covered with gel electrolyte; and the product was dried in an oven at 70° C. to prepare a pH reference electrode.

The flexible pH sensor was prepared by using the pH sensitive electrode obtained in step (2) and the pH reference electrode obtained in step (3).

Example 8

This example provides a preparation method for a flexible pH sensor. The flexible pH sensor includes a pH sensitive electrode and a pH reference electrode. Referring to FIG. 1, the method includes the following steps:

Step (1): Printing Electrodes

A 100 nm silver film was prepared on a PET substrate by a vapour deposition process and a 100 nm gold film was prepared on the silver film using the same process as the first electrode; and then, silver paste was stirred to be overprinted as a second electrode, where the printing substrate used was a flexible PET thin film.

Step (2): Preparation of pH Sensitive Electrode

As shown in (b) of FIG. 1, 50 ml of an electrolyte solution containing 2.45 g of sulfuric acid and 2.35 g of aniline was prepared. In an electrochemical workstation, cyclic voltammetry was adopted to prepare a polyaniline/silver ion composite material by using the first electrode prepared in step (1) as a working electrode, mercurous sulfate as a reference electrode, and a platinum wire as an counter electrode; the voltage was set to be within a range of −0.2 to 1.2 V, the scanning speed was 40-80 mV/s, and the number of cycles was 6-12 times; and the polyaniline/silver ion composite material was dried in an oven at 50-100° C. so as to obtain a pH sensitive electrode.

With respect to the scanning speed, the number of cycles and the subsequent oven temperature in the cyclic voltammetry during the preparation process of the pH sensitive electrode, this example conducted multiple experiments with different values, and finally the average value was taken as shown in Table 1.

Step (3): Preparation of pH Reference Electrode

As shown in (c) of FIG. 1, the second electrode prepared in step (1) was used as a working electrode, commercial silver/silver chloride was used as a reference electrode, and a platinum wire was used as an counter electrode; in 50 ml of a solution containing 0.48 g of hydrochloric acid, the voltage was set to be within a range of 0 to 0.2 V, and the scanning speed was set to 40 mV/s, with 4 cycles; then, as shown in (d) of FIG. 1, polyvinyl alcohol and potassium chloride were mixed together in a ratio of 1:1 (w/w), the mixture was stirred at 80° C. for 4 h, and the reference electrode was coated with the obtained mixture dropwise and frozen at −24° C. for 6 h to obtain a silver/silver chloride reference electrode covered with gel electrolyte; and the product was dried in an oven at 70° C. to prepare a pH reference electrode.

The flexible pH sensor was prepared by using the pH sensitive electrode obtained in step (2) and the pH reference electrode obtained in step (3).

Comparative Example 1

This comparative example provides a preparation method for a flexible pH sensor. The flexible pH sensor includes a pH sensitive electrode and a pH reference electrode. Referring to FIG. 1, the method includes the following steps:

Step (1): Printing Electrodes

First, a layer of silver paste was printed, and then a layer of carbon paste was printed after the silver paste was dried. The double-layer substrate was used as a first electrode, and then silver paste was stirred to be overprinted as a second electrode, where the printing substrate used was a flexible PET thin film.

Step (2): Preparation of pH Sensitive Electrode

As shown in (b) of FIG. 1, 50 ml of an electrolyte solution containing 1.27 g of sulfuric acid and 2.33 g of aniline was prepared. In an electrochemical workstation, cyclic voltammetry was adopted to prepare a polyaniline/silver ion composite material by using the first electrode prepared in step (1) as a working electrode, mercurous sulfate as a reference electrode, and a platinum wire as an counter electrode; the voltage was set to be within a range of −0.2 to 1.2 V, the scanning speed was 40-80 mV/s, and the number of cycles was 6-12 times; and the a polyaniline/silver ion composite material was dried in an oven at 50-100° C. so as to obtain a pH sensitive electrode.

With respect to the scanning speed, the number of cycles and the subsequent oven temperature in the cyclic voltammetry during the preparation process of the pH sensitive electrode, this example conducted multiple experiments with different values, and finally the average value was taken as shown in Table 1.

Step (3): Preparation of pH Reference Electrode

As shown in (c) of FIG. 1, the second electrode prepared in step (1) was used as a working electrode, commercial silver/silver chloride was used as a reference electrode, and a platinum wire was used as an counter electrode; in 50 ml of a solution containing 0.48 g of hydrochloric acid, the voltage was set to be within a range of 0 to 0.2 V, and the scanning speed was set to 20 mV/s, with 2 cycles; then, as shown in (d) of FIG. 1, polyvinyl alcohol and potassium chloride were mixed together in a ratio of 1:1 (w/w), the mixture was stirred at 80° C. for 4 h, and the reference electrode was coated with the obtained mixture dropwise and frozen at −26° C. for 4 h to obtain a silver/silver chloride reference electrode covered with gel electrolyte; and the product was dried in an oven at 70° C. to prepare a pH reference electrode.

The flexible pH sensor was prepared by using the pH sensitive electrode obtained in step (2) and the pH reference electrode obtained in step (3).

Comparative Example 2

This comparative example provides a preparation method for a flexible pH sensor. The flexible pH sensor includes a pH sensitive electrode and a pH reference electrode. Referring to FIG. 1, the method includes the following steps:

Step (1): Printing Electrodes

As shown in (a) of FIG. 1, composite paste formed by doping carbon paste with 10% (w/w) copper paste was printed as a first electrode, and then silver paste was stirred to be overprinted as a second electrode, where a printing substrate used was a flexible PET thin film.

Step (2): Preparation of pH Sensitive Electrode

As shown in (b) of FIG. 1, 50 ml of an electrolyte solution containing 1.27 g of sulfuric acid and 2.33 g of aniline was prepared. In an electrochemical workstation, cyclic voltammetry was adopted to prepare a polyaniline/copper ion composite material by using the first electrode prepared in step (1) as a working electrode, mercurous sulfate as a reference electrode, and a platinum wire as an counter electrode; the voltage was set to be within a range of −0.2 to 1.2 V, the scanning speed was 40-80 mV/s, and the number of cycles was 6-12 times; and the polyaniline/copper ion composite material was dried in an oven at 50-100° C. so as to obtain a pH sensitive electrode.

With respect to the scanning speed, the number of cycles and the subsequent oven temperature in the cyclic voltammetry during the preparation process of the pH sensitive electrode, this example conducted multiple experiments with different values, and finally the average value was taken as shown in Table 1.

Step (3): Preparation of pH Reference Electrode

As shown in (c) of FIG. 1, the second electrode prepared in step (1) was used as a working electrode, commercial silver/silver chloride was used as a reference electrode, and a platinum wire was used as an counter electrode; in 50 ml of a solution containing 0.48 g of hydrochloric acid, the voltage was set to be within a range of 0 to 0.2 V, and the scanning speed was set to 20 mV/s, with 2 cycles; then, as shown in (d) of FIG. 1, polyvinyl alcohol and potassium chloride were mixed together in a ratio of 1:1 (w/w), the mixture was stirred at 80° C. for 4 h, and the reference electrode was coated with the obtained mixture dropwise and frozen at −26° C. for 4 h to obtain a silver/silver chloride reference electrode covered with gel electrolyte; and the product was dried in an oven at 70° C. to prepare a pH reference electrode.

The flexible pH sensor was prepared by using the pH sensitive electrode obtained in step (2) and the pH reference electrode obtained in step (3).

Comparative Example 3

This comparative example provides a preparation method for a flexible pH sensor. The flexible pH sensor includes a pH sensitive electrode and a pH reference electrode. Referring to FIG. 1, the method includes the following steps:

Step (1): Printing Electrodes

As shown in (a) of FIG. 1, carbon paste was printed as a first electrode, and then silver paste was stirred to be overprinted as a second electrode, where a printing substrate used was a flexible PET thin film.

Step (2): Preparation of pH Sensitive Electrode

As shown in (b) of FIG. 1, 50 ml of an electrolyte solution containing 1.27 g of sulfuric acid and 2.33 g of aniline was prepared. In an electrochemical workstation, cyclic voltammetry was adopted to prepare a polyaniline material by using the first electrode prepared in step (1) as a working electrode, mercurous sulfate as a reference electrode, and a platinum wire as an counter electrode; the voltage was set to be within a range of −0.2 to 1.2 V, the scanning speed was 40-80 mV/s, and the number of cycles was 6-12 times; and the polyaniline material was dried in an oven at 50-100° C. so as to obtain a pH sensitive electrode.

With respect to the scanning speed, the number of cycles and the subsequent oven temperature in the cyclic voltammetry during the preparation process of the pH sensitive electrode, this example conducted multiple experiments with different values, and finally the average value was taken as shown in Table 1.

Step (3): Preparation of pH Reference Electrode

As shown in (c) of FIG. 1, the second electrode prepared in step (1) was used as a working electrode, commercial silver/silver chloride was used as a reference electrode, and a platinum wire was used as an counter electrode; in 50 ml of a solution containing 0.48 g of hydrochloric acid, the voltage was set to be within a range of 0 to 0.2 V, and the scanning speed was set to 20 mV/s, with 2 cycles; then, as shown in (d) of FIG. 1, polyvinyl alcohol and potassium chloride were mixed together in a ratio of 1:1 (w/w), the mixture was stirred at 80° C. for 4 h, and the reference electrode was coated with the obtained mixture dropwise and frozen at −26° C. for 4 h to obtain a silver/silver chloride reference electrode covered with gel electrolyte; and the product was dried in an oven at 70° C. to prepare a pH reference electrode.

The flexible pH sensor was prepared by using the pH sensitive electrode obtained in step (2) and the pH reference electrode obtained in step (3).

Comparative Example 4

This comparative example provides a preparation method for a flexible pH sensor. The flexible pH sensor includes a pH sensitive electrode and a pH reference electrode. Referring to FIG. 1, the method includes the following steps:

Step (1): Printing Electrodes

As shown in (a) of FIG. 1, carbon paste was printed as a first electrode, and then silver paste was stirred to be overprinted as a second electrode, where a printing substrate used was a flexible PET thin film.

Step (2): Preparation of pH sensitive electrode

As shown in (b) of FIG. 1, 50 ml of an electrolyte solution containing 1.27 g of sulfuric acid, 2.33 g of aniline, and 0.43 g of silver nitrate was prepared. In an electrochemical workstation, cyclic voltammetry was adopted to prepare a polyaniline/silver ion composite material by using the first electrode prepared in step (1) as a working electrode, mercurous sulfate as a reference electrode, and a platinum wire as an counter electrode; the voltage was set to be within a range of −0.2 to 1.2 V, the scanning speed was 40-80 mV/s, and the number of cycles was 6-12 times; and the polyaniline/silver ion composite material was dried in an oven at 50-100° C. so as to obtain a pH sensitive electrode.

With respect to the scanning speed, the number of cycles and the subsequent oven temperature in the cyclic voltammetry during the preparation process of the pH sensitive electrode, this example conducted multiple experiments with different values, and finally the average value was taken as shown in Table 1.

Step (3): Preparation of pH Reference Electrode

As shown in (c) of FIG. 1, the second electrode prepared in step (1) was used as a working electrode, commercial silver/silver chloride was used as a reference electrode, and a platinum wire was used as an counter electrode; in 50 ml of a solution containing 0.48 g of hydrochloric acid, the voltage was set to be within a range of 0 to 0.2 V, and the scanning speed was set to 20 mV/s, with 2 cycles; then, as shown in (d) of FIG. 1, polyvinyl alcohol and potassium chloride were mixed together in a ratio of 1:1 (w/w), the mixture was stirred at 80° C. for 4 h, and the reference electrode was coated with the obtained mixture dropwise and frozen at −26° C. for 4 h to obtain a silver/silver chloride reference electrode covered with gel electrolyte; and the product was dried in an oven at 70° C. to prepare a pH reference electrode.

The flexible pH sensor was prepared by using the pH sensitive electrode obtained in step (2) and the pH reference electrode obtained in step (3).

Test Example

The flexible pH sensor prepared by each of the examples and the comparative examples was tested for sensitivity, pH detection range and high bending stability. The test results are shown in Table 1.

In the tests, if the sensitivity of the sensor prepared with the pure carbon substrate in Comparative Example 3 was considered as 100%, the sensitivities of the sensors prepared in the other examples were compared therewith so as to obtain different percentages as relative sensitivity values.

TABLE 1

| | Relative sensitivity | pH detection range | High bending stability | Response time |
|---|---|---|---|---|
| Example 1 | 130.2% | 2-12 | Good | 8 s |
| Example 2 | 128.3% | 2-12 | Good | 10 s |
| Example 3 | 108.3% | 2-12 | Good | 33 s |
| Example 4 | 109.0% | 2-12 | Good | 30 s |
| Example 5 | 105.5% | 2-12 | Good | 47 s |
| Example 6 | 101.2% | 2-12 | Good | 3 s |
| Example 7 | 111.2% | 2-12 | Good | 13 s |
| Example 8 | 120.7% | 2-12 | Good | 4 s |
| Comparative Example 1 | 115.1% | 2-12 | Good | 11 s |
| Comparative Example 2 | 62.7% | 2-12 | Good | 23 s |
| Comparative Example 3 | 100.0% | 2-12 | Good | 41 s |
| Comparative Example 4 | 115.4% | 2-12 | Good | 14 s |

As can be seen from Table 1, the pH sensors prepared in all the examples have better high bending stability (defined as polyaniline not falling off after bending, with a voltage change being within 10% after bending), the pH detection ranges of the pH sensors can reach up to 2-12, and the sensitivity and response time of the pH sensors are both improved compared to those of pH sensors prepared without doping with metal ions. The relative pH sensitivity of the pH sensor prepared by doping with silver ions is 130.2%, and the reaction time at pH 4-8 is 10 s, so that the effect is very good.

Application Example

Figure 2:
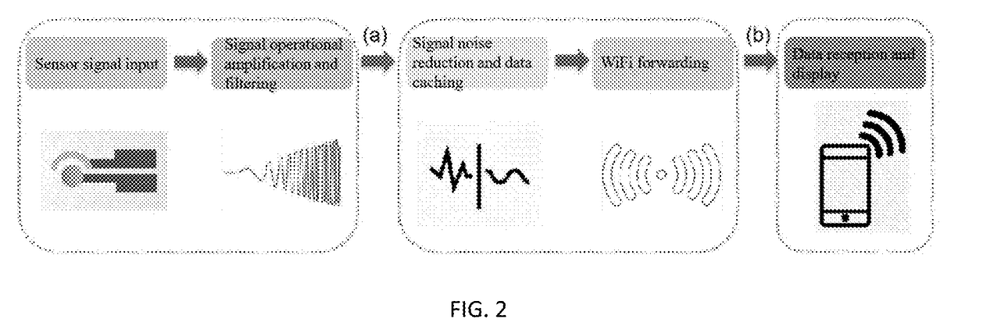
FIG. 2 is a schematic diagram of an all-solid system according to the present disclosure.

This application example provides a flexible pH detection system, the flexible pH detection system includes the above-mentioned flexible pH sensor, an external circuit, and a program development and interface; the external circuit achieves a connection between the pH sensor and an analog-to-digital conversion module with an external wire, the connection part therebetween is fixed by spot welding, the analog-to-digital conversion module is connected to an analog channel of a development board by ways of a wire, and received pH sensor signals are transmitted to the development board through the analog channel. The data quantity received by the development board is computed and processed so as to be output as a pH value. After operational amplification and filtering, signal noise reduction is performed. After caching, the result is forwarded through a communication module. Finally, the pH value result is received by a mobile phone terminal and then displayed through a mobile phone terminal interface, as shown in FIG. 2.

During use, the above-mentioned flexible pH sensor is placed in a saliva sample or a fresh food packaging box, so as to obtain the pH value of the sample in real time.

The program development and interface mainly use some data frames and curve charts for real-time display of changes in pH and voltage. Furthermore, an operation interface can also show the situation reflected by the pH value under the corresponding scene and give a corresponding suggestion. For example, when it is used to detect the pH value of a saliva sample, the current tooth health status and suggestions given under different health conditions will be shown on the operation interface; and when it is used to detect the pH value of a fresh food sample, the freshness of fresh food at different pH values will be shown on the operation interface. When test equipment and a mobile phone are in the same wireless local area network, the connection with a cloud server is achieved by an MQTT protocol, and both parties upload data to the cloud server for data communication. The sensitivity of the obtained device is 110.3%, the reaction time is 10 s, and obtained device has good flexibility and reusability.

Some steps mentioned in the examples of the present disclosure may be implemented using software, and corresponding software programs may be stored in readable storage media, such as optical disks or hard disks.

The foregoing descriptions are merely exemplary examples of the present disclosure, and are not intended to limit the present disclosure. Any modifications, equivalent substitutions, improvements, and the like made within the spirit and principles of the present disclosure shall be included within the scope of protection of the present disclosure.

What is claimed is:

1. A preparation method for a flexible pH sensor, wherein the flexible pH sensor comprises a pH sensitive electrode and a pH reference electrode, wherein the preparation method of the pH sensitive electrode comprises:
    step (1): preparing a first electrode by using a composite conductive material as a conductive layer and a flexible thin film as a substrate, wherein the composite conductive material comprises two conductive materials, respectively; and
    step (2): preparing an electrolyte solution containing an acid and aniline, adopting cyclic voltammetry to prepare a polyaniline/cation composite material by using the first electrode prepared in step (1) as a working electrode in combination with a reference electrode and a counter electrode, and drying the deposited polyaniline/cation composite on the first electrode to obtain the pH sensitive electrode;
    wherein one of the conductive materials in step (1) is a material that does not react with the electrolyte solution and serves as a growth substrate for polyaniline; and the other conductive material in step (1) is an insoluble and easily electrolyzed material that is oxidized after being applied with voltage during the cyclic voltammetry so as to provide cations for the polyaniline/cation composite material;

wherein the conductive material that does not react with the electrolyte comprises carbon, FTO, platinum, or gold;

wherein the other conductive material comprises one or more of silver, aluminum, iron, tungsten, zinc, and calcium.

2. The preparation method according to claim 1, wherein in the composite conductive material, a mass ratio of the conductive material to the other conductive material is (3-20):1.

3. The preparation method according to claim 1, wherein the acid is selected from the group consisting of sulfuric acid, hydrochloric acid, phosphoric acid, oxalic acid, dodecylbenzene sulfonic acid, or salicylic acid.

* * * * *